US012618826B2

(12) United States Patent
Mitnick et al.

(10) Patent No.: US 12,618,826 B2
(45) Date of Patent: *May 5, 2026

(54) MULTI-CHIP PACKAGING OF INTEGRATED CIRCUITS AND FLOW CELLS FOR NANOPORE SEQUENCING

(71) Applicant: Roche Sequencing Solutions, Inc., Pleasanton, CA (US)

(72) Inventors: Yuri Mitnick, San Jose, CA (US); Xu Ouyang, Cupertino, CA (US); Janusz B. Wojtowicz, Sunnyvale, CA (US)

(73) Assignee: Roche Sequencing Solutions, Inc., Pleasanton, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/603,061

(22) Filed: Mar. 12, 2024

(65) Prior Publication Data

US 2024/0219369 A1 Jul. 4, 2024

Related U.S. Application Data

(63) Continuation of application No. 17/457,843, filed on Dec. 6, 2021, now Pat. No. 11,953,494, which is a
(Continued)

(51) Int. Cl.
*G01N 33/487* (2006.01)
*B01L 3/00* (2006.01)
(Continued)

(52) U.S. Cl.
CPC .. *G01N 33/48721* (2013.01); *B01L 3/502715* (2013.01); *C12Q 1/6869* (2013.01);
(Continued)

(58) Field of Classification Search
CPC ......... G01N 27/44791; G01N 27/4473; G01N 27/48707; G01N 27/48735;
(Continued)

(56) References Cited

U.S. PATENT DOCUMENTS 11,193,922 B2    12/2021    Mitnick et al.
11,953,494 B2 *   4/2024    Mitnick ........... G01N 33/48721
(Continued)

FOREIGN PATENT DOCUMENTS

CN          1202929 A     12/1998
CN          1552887 A     12/2004
(Continued)

OTHER PUBLICATIONS

International Search Report & Written Opinion mailed on Feb. 6, 2018 in corresponding PCT application No. PCT/EP2017/077107 filed on Oct. 24, 2017, pp. 1-11.

*Primary Examiner* — Gurpreet Kaur
(74) *Attorney, Agent, or Firm* — Winston Chu

(57) ABSTRACT

A nanopore-based sequencing system includes a plurality of nanopore-based sequencing chips. Each of the nanopore-based sequencing chips comprises a plurality of nanopore sensors. The system comprises at least one flow cell coupled to at least one of the plurality of nanopore-based sequencing chips, wherein the flow cell coupled to the at least one of the plurality of nanopore-based sequencing chips comprises one or more fluidic flow channels that allow a fluid external to the system to flow on top of the nanopore-based sequencing chip and out of the system. The system further comprises a printed circuit board electrically connected to the plurality of nanopore-based sequencing chips.

11 Claims, 11 Drawing Sheets

Related U.S. Application Data continuation of application No. 16/394,962, filed on Apr. 25, 2019, now Pat. No. 11,193,922, which is a continuation of application No. PCT/EP2017/077107, filed on Oct. 24, 2017.

(60) Provisional application No. 62/413,336, filed on Oct. 26, 2016.

(51) Int. Cl.
| | |
|---|---|
| *C12Q 1/6869* | (2018.01) |
| *G01N 27/447* | (2006.01) |

(52) U.S. Cl.
CPC .. *G01N 27/44791* (2013.01); *B01L 2200/027* (2013.01); *B01L 2300/0636* (2013.01)

(58) Field of Classification Search
CPC ............. Y10S 977/852; Y10S 977/733; Y10S 977/72; Y10S 977/721; B01L 2300/0636; B01L 3/502715; B01L 2200/027; C12Q 2563/116; C12Q 2565/63
See application file for complete search history.

(56) References Cited

U.S. PATENT DOCUMENTS

| | | |
|---|---|---|
| 2007/0202008 A1 | 8/2007 | Schembri et al. |
| 2010/0324392 A1 | 12/2010 | Yee et al. |
| 2010/0327847 A1 | 12/2010 | Leiber et al. |
| 2011/0275522 A1 | 11/2011 | Rothberg et al. |
| 2012/0322679 A1 | 12/2012 | Brown et al. |
| 2013/0217106 A1 | 8/2013 | Jones |
| 2014/0021047 A1* | 1/2014 | Shim ..................... B82Y 15/00 |
| | | 204/601 |
| 2014/0034497 A1 | 2/2014 | Davis et al. |
| 2014/0158540 A1 | 6/2014 | Ohura |
| 2014/0174927 A1 | 6/2014 | Bashir et al. |
| 2014/0190833 A1 | 7/2014 | Lieber et al. |
| 2015/0021187 A1 | 1/2015 | Lin et al. |
| 2015/0041324 A1* | 2/2015 | Jeon ................. B01L 3/502707 |
| | | 204/601 |
| 2016/0146203 A1 | 5/2016 | Yuan |
| 2016/0178576 A1 | 6/2016 | Maney et al. |
| 2016/0274082 A1* | 9/2016 | Yuan .................... C12Q 1/6869 |
| 2017/0283867 A1 | 10/2017 | Wahba et al. |
| 2017/0370903 A1 | 12/2017 | Mager et al. |

FOREIGN PATENT DOCUMENTS

| | | |
|---|---|---|
| CN | 1687391 A | 10/2005 |
| CN | 104011866 A | 8/2014 |
| CN | 102307517 B | 10/2014 |
| CN | 103370617 B | 11/2015 |
| CN | 102741430 B | 7/2016 |
| CN | 103842519 B | 2/2018 |
| EP | 2157165 A1 | 2/2010 |
| JP | 2007010428 A | 1/2007 |
| JP | 2012225770 A | 11/2012 |
| JP | 2013036865 A | 2/2013 |
| JP | 2015-525077 A | 9/2015 |
| WO | 9712030 A1 | 4/1997 |
| WO | 2007145228 A1 | 12/2007 |
| WO | 2011097028 A1 | 8/2011 |
| WO | 2013188841 A1 | 12/2013 |
| WO | 2014/064443 A2 | 5/2014 |
| WO | 2016/059417 A1 | 4/2016 |
| WO | 2016/099672 A1 | 6/2016 |

* cited by examiner

100

600

608

608

610

610

610

606

606

602

608

604

MULTI-CHIP PACKAGING OF INTEGRATED CIRCUITS AND FLOW CELLS FOR NANOPORE SEQUENCING

CROSS REFERENCE TO RELATED APPLICATIONS

This application is a continuation of U.S. patent application Ser. No. 17/457,843, filed Dec. 5, 2021, which is a continuation of U.S. patent application Ser. No. 16/394,962, filed Apr. 4, 25, 2019, which is a continuation of International Application No. PCT/EP2017/077107, filed Oct. 24, 2017, which claims priority to U.S. Provisional Application No. 62/413,336, filed Oct. 26, 2016, each of which is herein incorporated by reference in its entirety.

BACKGROUND OF THE INVENTION

Advances in micro-miniaturization within the semiconductor industry in recent years have enabled biotechnologists to begin packing traditionally bulky sensing tools into smaller and smaller form factors, onto so-called biochips. It would be desirable to develop techniques for biochips that make them more robust, efficient, and cost-effective.

BRIEF DESCRIPTION OF THE INVENTION

In a first aspect, the present invention provides a nanopore-based sequencing system, comprising a plurality of nanopore-based sequencing chips, each of the nanopore-based sequencing chips comprising a plurality of nanopore sensors; at least one flow cell coupled to at least one of the plurality of nanopore-based sequencing chips, wherein the flow cell coupled to the at least one of the plurality of nanopore-based sequencing chips comprises one or more fluidic flow channels that allow a fluid external to the system to flow on top of the nanopore-based sequencing chip and out of the system; and a printed circuit board electrically connected to the plurality of nanopore-based sequencing chips.

The at least one flow cell may be coupled to at least two of the plurality of nanopore-based sequencing chips and at least one flow cell may be connected to an inlet, an outlet, and a fluidic pump. The one or more fluidic flow channels may direct fluid to flow across a chip-to-chip boundary, wherein the chip-to-chip boundary is a boundary between the at least two of the plurality of nanopore-based sequencing chips. The chip-to-chip boundary may be hermetically sealed, for example by dicing side walls of the at least two of the plurality of nanopore-based sequencing chips to be substantially vertical and flat; placing the side walls of the at least two of the plurality of nanopore-based sequencing chips such that the side walls are butted against each other; and depositing a hermetic sealing material on the side walls. The chip-to-chip boundary may also be hermetically sealed by bonding the at least two of the plurality of nanopore-based sequencing chips onto the at least one flow cell. The at least one flow cell may comprises a molded pliable material or a glass material.

At least one of the plurality of nanopore-based sequencing chips may comprise a bonding surface bonding to the at least one flow cell, wherein the bonding surface does not include circuitry or other components. The nanopore-based sequencing system or instrument may further comprise a plurality of bond wires, wherein the printed circuit board may further comprise a plurality of metal connectors, and the plurality of bond wires may electrically connect at least one of the plurality of nanopore-based sequencing chips to at least some of the plurality of metal connectors, and the plurality of bond wires may arch upwards and do not touch one another. The nanopore-based sequencing system may further comprise an encapsulation layer covering the plurality of bond wires.

The plurality of nanopore-based sequencing chips may be embedded in the printed circuit board, and the printed circuit board may further comprise a plurality of metal connectors, and at least one of the plurality of metal connectors may have a portion that lies flat on a top surface of the printed circuit board and that lies flat on a top surface of one of the plurality of nanopore-based sequencing chips, and the at least one of the plurality of metal connectors may be electrically connected to the one of the plurality of nanopore-based sequencing chips. The system or instrument may further comprise an encapsulation layer, wherein the portion that lies flat on the top surface of the printed circuit board and that lies flat on the top surface of the one of the plurality of nanopore-based sequencing chips is covered by the encapsulation layer.

The printed circuit board may comprise a plurality of cavities, and the at least one of the plurality of nanopore-based sequencing chips may be positioned right-side up and below the printed circuit board such that the plurality of nanopore sensors of the nanopore-based sequencing chip are exposed by one of the plurality of cavities. Then, the at least one flow cell is embedded in a well formed by the one of the plurality of cavities and the at least one of the plurality of nanopore-based sequencing chips.

In a second aspect, the present invention provides a method of integrating a nanopore-based sequencing system, comprising: coupling at least one flow cell to at least one of a plurality of nanopore-based sequencing chips, wherein the flow cell coupled to the at least one of the plurality of nanopore-based sequencing chips comprises one or more fluidic flow channels that allow a fluid external to the system to flow on top of the nanopore-based sequencing chip and out of the system, and wherein each of the nanopore-based sequencing chips comprises a plurality of nanopore sensors; and electrically connecting a printed circuit board to the plurality of nanopore-based sequencing chips.

The method may comprise coupling the at least one flow cell to at least two of the plurality of nanopore-based sequencing chips, and optionally connecting the at least one flow cell to an inlet, an outlet, and a fluidic pump. The one or more fluidic flow channels may direct fluid to flow across a prefer chip-to-chip boundary, wherein the chip-to-chip boundary is a boundary between the at least two of the plurality of nanopore-based sequencing chips, and wherein said boundary may be hermetically sealed. Said hermetically sealing the chip-to-chip boundary may comprise dicing side walls of the at least two of the plurality of nanopore-based sequencing chips to be substantially vertical and flat; placing the side walls of the at least two of the plurality of nanopore-based sequencing chips such that the side walls are butted against each other; and depositing a hermetic sealing material on the side walls. Alternatively, said hermetically sealing the chip-to-chip boundary may comprise bonding the at least two of the plurality of nanopore-based sequencing chips onto the at least one flow cell.

The method may also comprise molding the at least one flow cell using a pliable material, or using a glass material. The method may also comprise bonding a bonding surface of the at least one of the plurality of nanopore-based sequencing chips to the at least one flow cell, wherein the bonding surface does not include circuitry or other components.

The method may also comprise electrically connecting the at least one of the plurality of nanopore-based sequencing chips to at least some of a plurality of metal connectors of the printed circuit board using a plurality of bond wires, wherein the plurality of bond wires arch upwards and do not touch one another, and optionally covering the plurality of bond wires using an encapsulation layer.

The method may also comprise embedding the plurality of nanopore-based sequencing chips in the printed circuit board, wherein the printed circuit board further comprises a plurality of metal connectors, and wherein at least one of the plurality of metal connectors has a portion that lies flat on a top surface of the printed circuit board and that lies flat on a top surface of one of the plurality of nanopore-based sequencing chips, and wherein the at least one of the plurality of metal connectors is electrically connected to the one of the plurality of nanopore-based sequencing chips. Then, method may in addition comprise covering the portion that lies flat on the top surface of the printed circuit board and that lies flat on the top surface of the one of the plurality of nanopore-based sequencing chips by an encapsulation layer.

If the printed circuit board comprises a plurality of cavities, the method may also comprise positioning the at least one of the plurality of nanopore-based sequencing chips right-side up and below the printed circuit board such that the plurality of nanopore sensors of the nanopore-based sequencing chip are exposed by one of the plurality of cavities. Then, the at least one flow cell may be embedded in a well formed by the one of the plurality of cavities and the at least one of the plurality of nanopore-based sequencing chips.

BRIEF DESCRIPTION OF THE DRAWINGS

Various embodiments of the invention are disclosed in the following detailed description and the accompanying drawings.

DETAILED DESCRIPTION

The invention can be implemented in numerous ways, including as a process; an apparatus; a system; a composition of matter; a computer program product embodied on a computer readable storage medium; and/or a processor, such as a processor configured to execute instructions stored on and/or provided by a memory coupled to the processor. In this specification, these implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions.

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

Nanopore membrane devices having pore sizes on the order of one nanometer in internal diameter have shown promise in rapid nucleotide sequencing. When a voltage potential is applied across a nanopore immersed in a conducting fluid, a small ion current attributed to the conduction of ions through the nanopore can be observed. The size of the current is sensitive to the pore size.

A nanopore-based sequencing chip may be used for nucleic acid (e.g., DNA) sequencing. A nanopore-based sequencing chip incorporates a large number of sensor cells configured as an array. For example, an array of one million cells may include 1000 rows by 1000 columns of cells.

Figure 1:
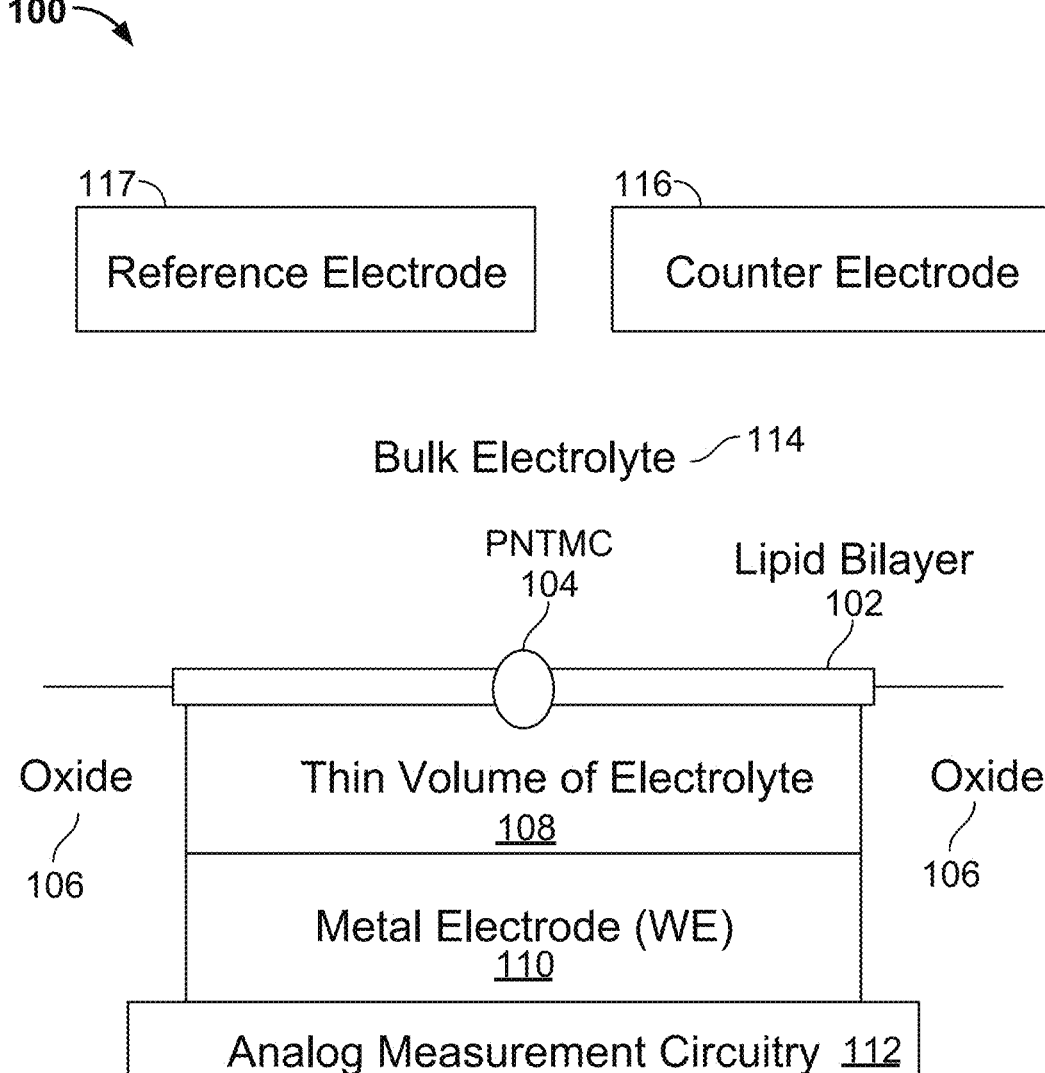
FIG. 1 illustrates an embodiment of a cell 100 in a nanopore-based sequencing chip.

FIG. 1 illustrates an embodiment of a cell 100 in a nanopore-based sequencing chip. A membrane 102 is formed over the surface of the cell. In some embodiments, membrane 102 is a lipid bilayer. The bulk electrolyte 114 containing soluble protein nanopore transmembrane molecular complexes (PNTMC) and the analyte of interest is placed directly onto the surface of the cell. In one embodiment, a single PNTMC 104 is inserted into membrane 102 by electroporation. The individual membranes in the array are neither chemically nor electrically connected to each other. Thus, each cell in the array is an independent sequencing machine, producing data unique to the single polymer molecule associated with the PNTMC. PNTMC 104 operates on the analytes and modulates the ionic current through the otherwise impermeable bilayer.

With continued reference to FIG. 1, analog measurement circuitry 112 is connected to a metal electrode 110 covered by a volume of electrolyte 108. The volume of electrolyte 108 is isolated from the bulk electrolyte 114 by the ion-impermeable membrane 102. PNTMC 104 crosses membrane 102 and provides the only path for ionic current to flow from the bulk liquid to working electrode 110. The cell also includes a counter electrode (CE) 116, which is in electrical contact with the bulk electrolyte 114. The cell may also include a reference electrode 117.

Figure 2:
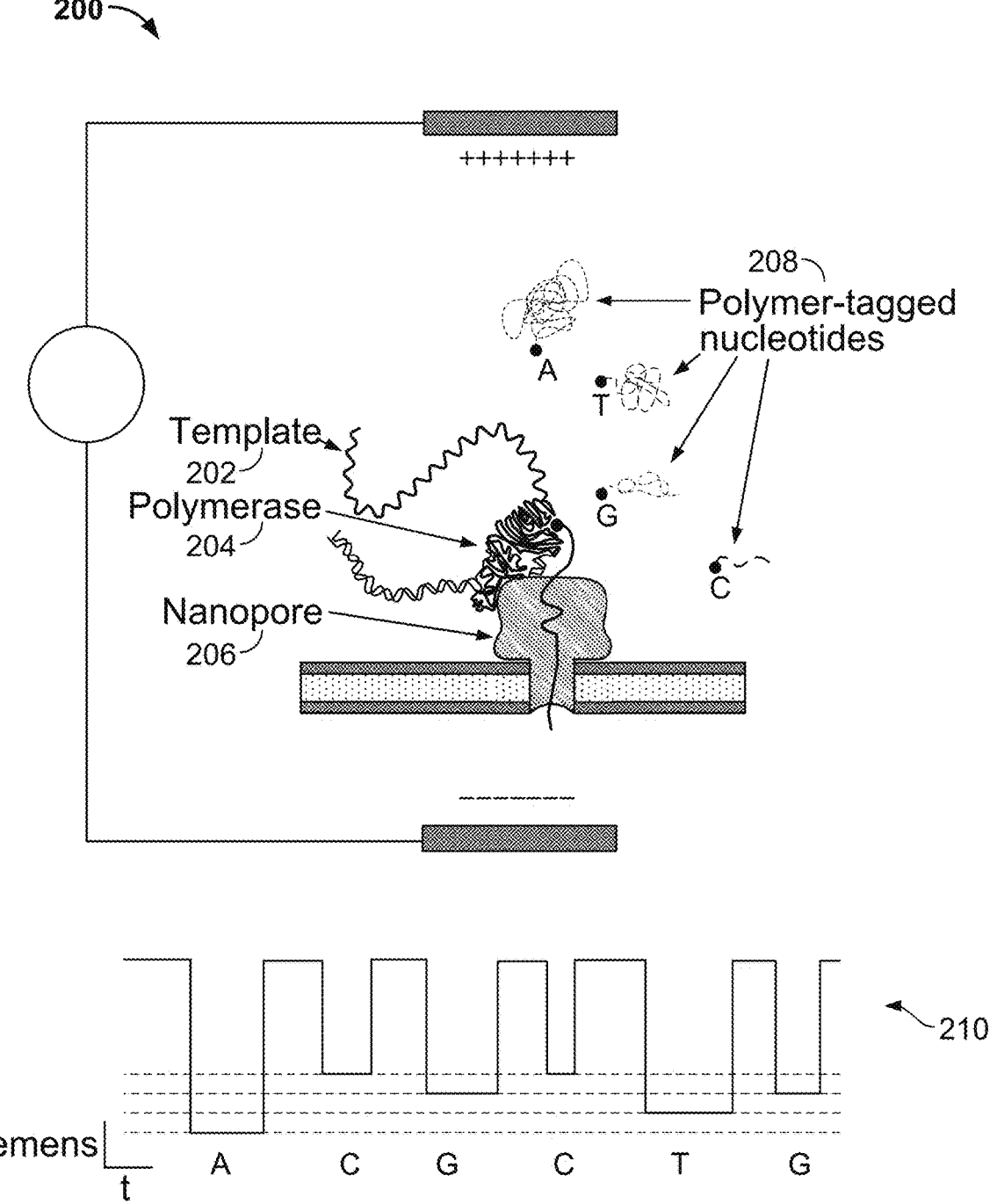
FIG. 2 illustrates an embodiment of a cell 200 performing nucleotide sequencing with the Nano-SBS technique.

In some embodiments, a nanopore array enables parallel sequencing using the single molecule nanopore-based sequencing by synthesis (Nano-SBS) technique. FIG. 2 illustrates an embodiment of a cell 200 performing nucleotide sequencing with the Nano-SBS technique. In the Nano-SBS technique, a template 202 to be sequenced and a primer are introduced to cell 200. To this template-primer complex, four differently tagged nucleotides 208 are added to the bulk aqueous phase. As the correctly tagged nucleotide is complexed with the polymerase 204, the tail of the tag is positioned in the barrel of nanopore 206. The tag held in the barrel of nanopore 206 generates a unique ionic blockade signal 210, thereby electronically identifying the added base due to the tags' distinct chemical structures.

Figure 3:
FIG. 3 illustrates an embodiment of a cell about to perform nucleotide sequencing with pre-loaded tags.
Figure 3:
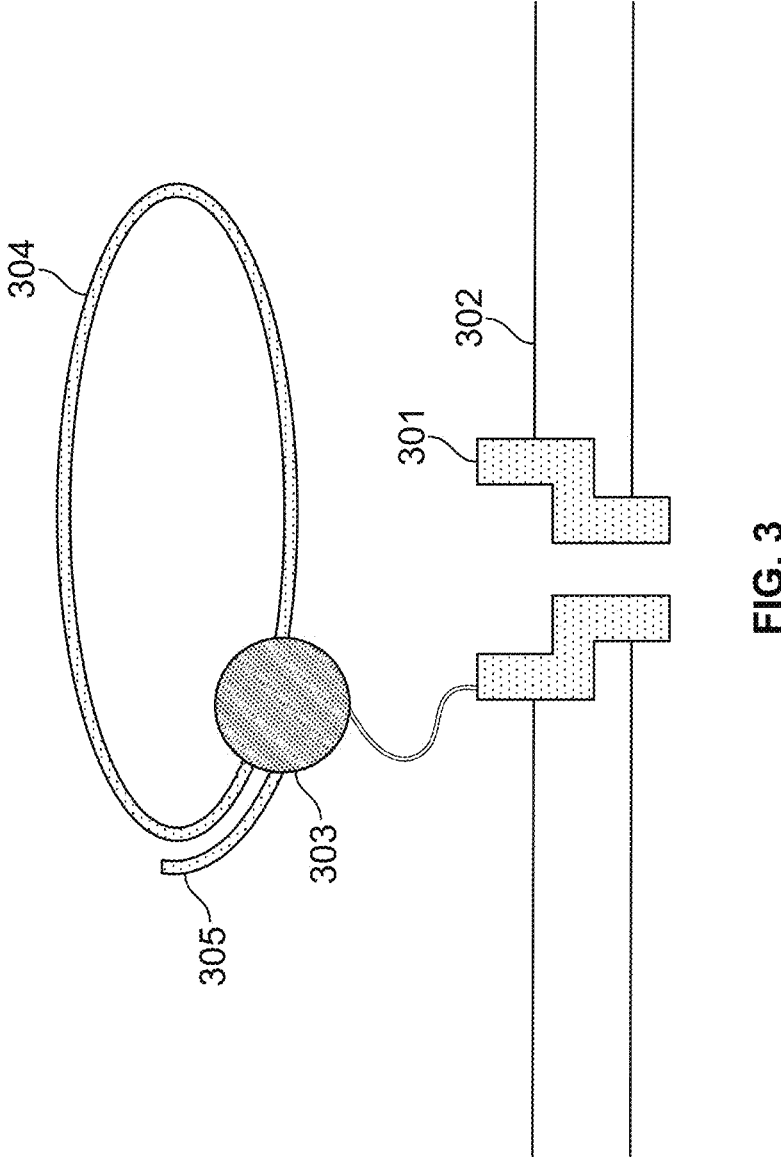

FIG. 3 illustrates an embodiment of a cell about to perform nucleotide sequencing with pre-loaded tags. A nanopore 301 is formed in a membrane 302. An enzyme 303 (e.g., a polymerase, such as a DNA polymerase) is associated with the nanopore. In some cases, polymerase 303 is covalently attached to nanopore 301. Polymerase 303 is associated with a nucleic acid molecule 304 to be sequenced. In some embodiments, the nucleic acid molecule 304 is circular. In some cases, nucleic acid molecule 304 is linear. In some embodiments, a nucleic acid primer 305 is hybridized to a portion of nucleic acid molecule 304. Polymerase 303 catalyzes the incorporation of nucleotides 306 onto primer 305 using single stranded nucleic acid molecule 304 as a template. Nucleotides 306 comprise tag species ("tags") 307.

Figure 4:
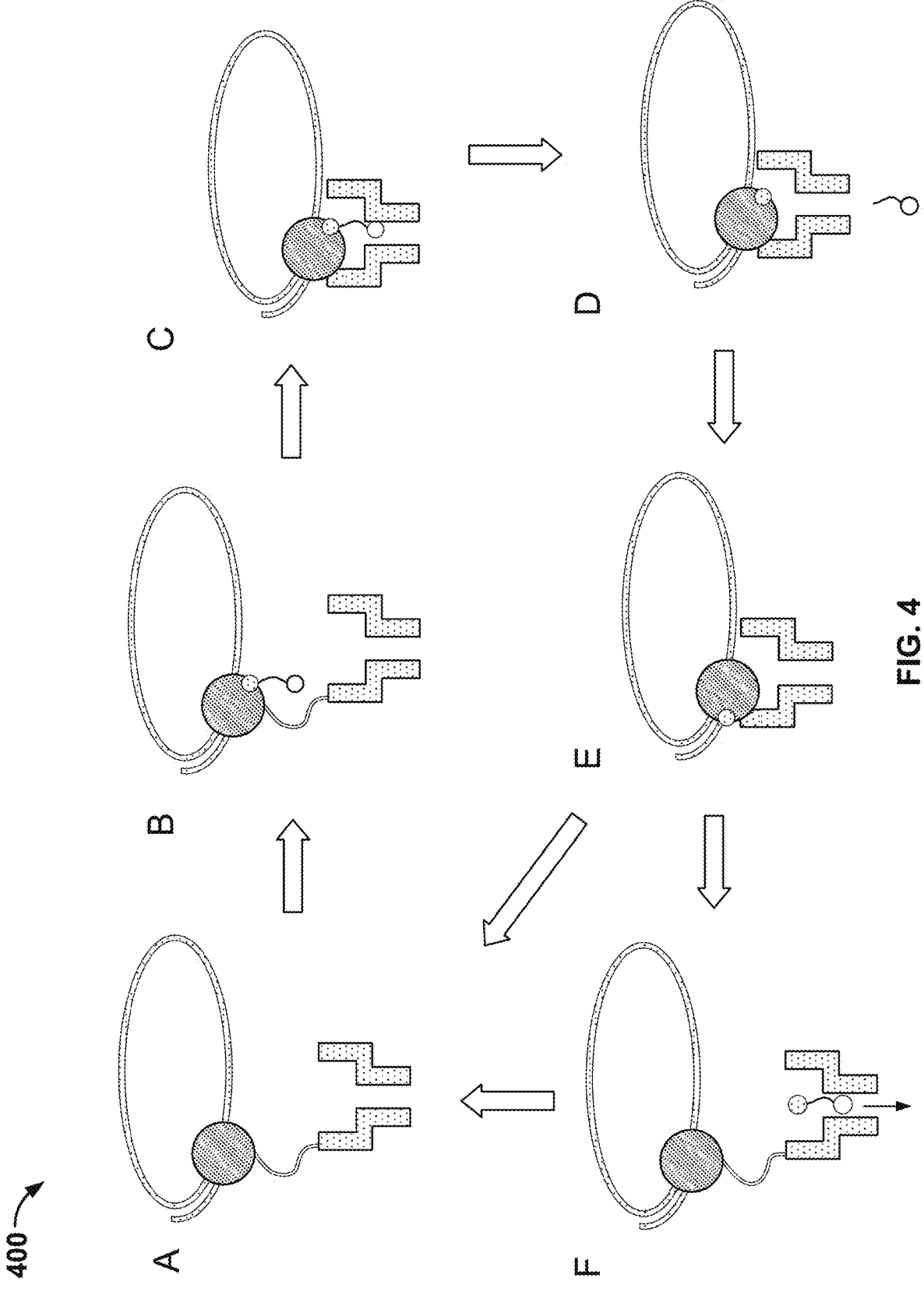
FIG. 4 illustrates an embodiment of a process 400 for nucleic acid sequencing with pre-loaded tags.

FIG. 4 illustrates an embodiment of a process 400 for nucleic acid sequencing with pre-loaded tags. Stage A illustrates the components as described in FIG. 3. Stage C shows the tag loaded into the nanopore. A "loaded" tag may be one that is positioned in and/or remains in or near the nanopore for an appreciable amount of time, e.g., 0.1 millisecond (ms) to 10,000 ms. In some cases, a tag that is pre-loaded is loaded in the nanopore prior to being released from the nucleotide. In some instances, a tag is pre-loaded if the probability of the tag passing through (and/or being detected by) the nanopore after being released upon a nucleotide incorporation event is suitably high, e.g., 90% to 99%.

At stage A, a tagged nucleotide (one of four different types: A, T, G, or C) is not associated with the polymerase. At stage B, a tagged nucleotide is associated with the polymerase. At stage C, the polymerase is docked to the nanopore. The tag is pulled into the nanopore during docking by an electrical force, such as a force generated in the presence of an electric field generated by a voltage applied across the membrane and/or the nanopore.

Some of the associated tagged nucleotides are not base paired with the nucleic acid molecule. These non-paired nucleotides typically are rejected by the polymerase within a time scale that is shorter than the time scale for which correctly paired nucleotides remain associated with the polymerase. Since the non-paired nucleotides are only transiently associated with the polymerase, process 400 as shown in FIG. 4 typically does not proceed beyond stage D. For example, a non-paired nucleotide is rejected by the polymerase at stage B or shortly after the process enters stage C.

Before the polymerase is docked to the nanopore, the conductance of the nanopore is ~300 picosiemens (300 pS). At stage C, the conductance of the nanopore is about 60 pS, 80 pS, 100 pS, or 120 pS, corresponding to one of the four types of tagged nucleotides respectively. The polymerase undergoes an isomerization and a transphosphorylation reaction to incorporate the nucleotide into the growing nucleic acid molecule and release the tag molecule. In particular, as the tag is held in the nanopore, a unique conductance signal (e.g., see signal 210 in FIG. 2) is generated due to the tag's distinct chemical structures, thereby identifying the added base electronically. Repeating the cycle (i.e., stage A through E or stage A through F) allows for the sequencing of the nucleic acid molecule. At stage D, the released tag passes through the nanopore.

In some cases, tagged nucleotides that are not incorporated into the growing nucleic acid molecule will also pass through the nanopore, as seen in stage F of FIG. 4. The unincorporated nucleotide can be detected by the nanopore in some instances, but the method provides a means for distinguishing between an incorporated nucleotide and an unincorporated nucleotide based at least in part on the time for which the nucleotide is detected in the nanopore. Tags bound to unincorporated nucleotides pass through the nanopore quickly and are detected for a short period of time (e.g., less than 10 ms), while tags bound to incorporated nucleotides are loaded into the nanopore and detected for a long period of time (e.g., at least 10 ms).

Figure 5:
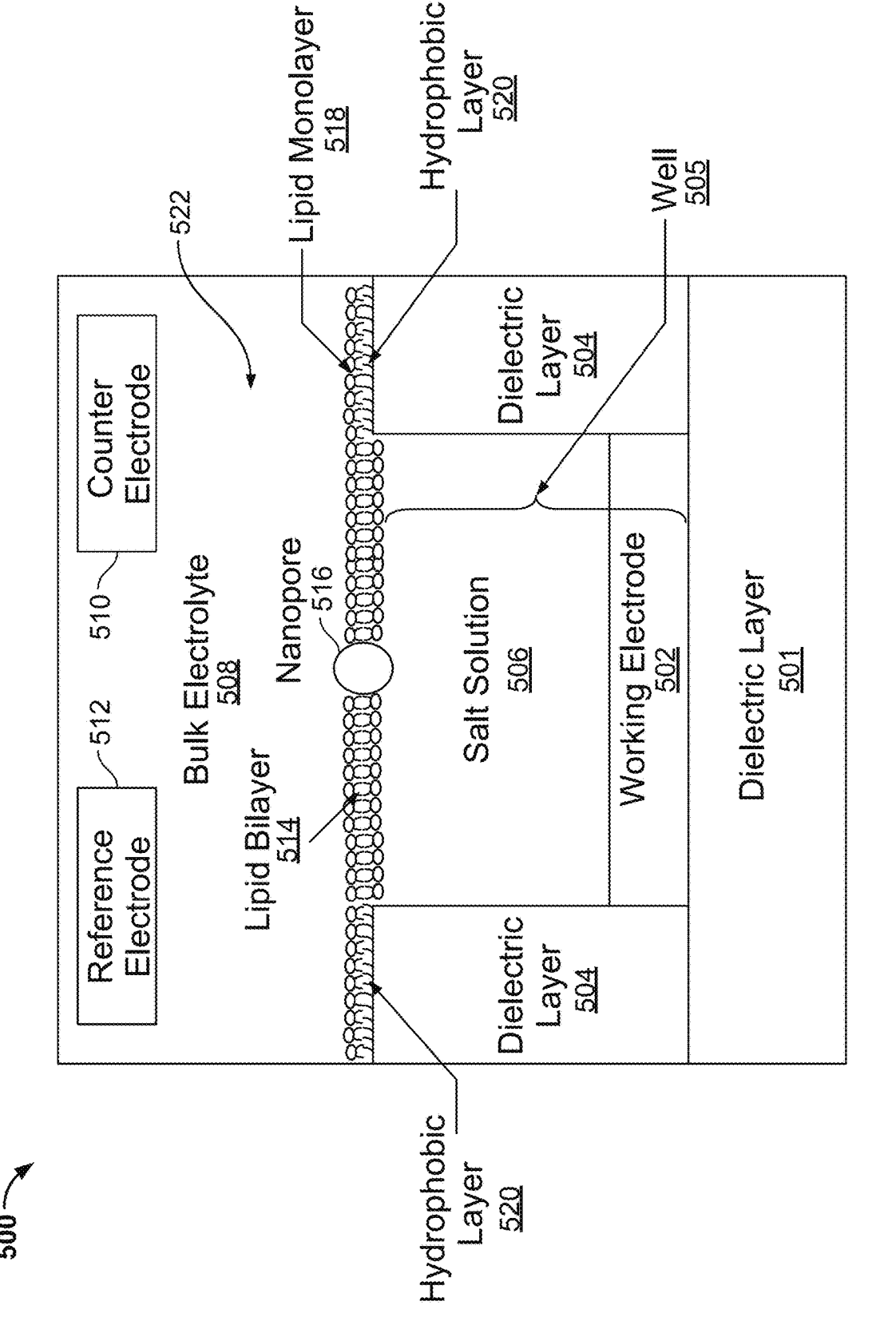
FIG. 5 illustrates an embodiment of a cell 500 in a nanopore-based sequencing chip.

FIG. 5 illustrates an embodiment of a cell 500 in a nanopore-based sequencing chip. Cell 500 includes a well 505 having two side walls and a bottom. In one embodiment, each side wall comprises a dielectric layer 504 and the bottom comprises a working electrode 502. In one embodiment, the working electrode 502 has a top side and a bottom side. In another embodiment, the top side of 502 makes up the bottom of the well 505 while the bottom side of 502 is in contact with dielectric layer 501. In another embodiment, the dielectric layer 504 is above dielectric layer 501. Dielectric layer 504 forms the walls surrounding a well 505 in which a working electrode 502 is located at the bottom. Suitable dielectric materials for use in the present invention (e.g., dielectric layer 501 or 504) include, without limitation, porcelain (ceramic), glass, mica, plastics, oxides, nitrides (e.g., silicon mononitride or SiN), silicon oxynitride, metal oxides, metal nitrides, metal silicates, transition-metal oxides, transition-metal nitrides, transition metal-silicates, oxynitrides of metals, metal aluminates, zirconium silicate, zirconium aluminate, hafnium oxide, insulating materials (e.g., polymers, epoxies, photoresist, and the like), or combinations thereof. Those of ordinary skill in the art will appreciate other dielectric materials that are suitable for use in the present invention.

In one aspect, cell 500 also includes one or more hydrophobic layers. As shown in FIG. 5, each dielectric layer 504 has a top surface. In one embodiment, the top surface of each dielectric layer 504 may comprise a hydrophobic layer. In one embodiment, silanization forms a hydrophobic layer 520 above the top surface of dielectric layer 504. For example, further silanization with silane molecules (i) containing 6 to 20 carbon-long chains (e.g., octadecyl-trichlorosilane, octadecyl-trimethoxysilane, or octadecyl-triethoxysilane), (ii) dimethyloctylchlorosilane (DMOC), or (iii) organofunctional alkoxysilane molecules (e.g., dimethyl-chloro-octodecyl-silane, methyldichloro-octodecyl-silane, trichloro-octodecyl-silane, trimethyl-octodecyl-silane, or triethyl-octodecyl-silane) can be done on the top surface of dielectric layer 504. In one embodiment, the hydrophobic layer is a silanized layer or silane layer. In one embodiment, the silane layer can be one molecule in thickness. In one aspect, dielectric layer 504 comprises a top surface suitable for adhesion of a membrane (e.g., a lipid bilayer comprising a nanopore). In one embodiment, the top surface suitable for adhesion of a membrane comprises a silane molecule as described herein. In some embodiments, hydrophobic layer 520 has a thickness provided in a nanometer (nM) or micrometer (μm) scale. In other embodiments, the hydrophobic layer may extend down along all or a part of the dielectric layer 504. (see also Davis et al. U.S. 20140034497, which is incorporated herein by reference in its entirety).

In another aspect, well 505 (formed by the dielectric layer walls 504) further includes a volume of salt solution 506 above working electrode 502. In general, the methods of the present invention comprise the use of a solution (e.g., a salt solution, salt buffer solution, electrolyte, electrolyte solution, or bulk electrolyte) that comprises osmolytes. As used herein, the term "osmolyte" refers to any soluble compound that when dissolved into solution increases the osmolarity of that solution. In the present invention, an osmolyte is a compound that is soluble in solution within the architecture of a nanopore sequencing system, e.g., a well containing a salt solution or a bulk electrolyte as described herein. As such, the osmolytes of the present invention affect osmosis, particularly osmosis across a lipid bilayer. Osmolytes for use in the present invention include, without limitation, ionic salts such as lithium chloride (LiCl), sodium chloride (NaCl), potassium chloride (KCl), lithium glutamate, sodium glutamate, potassium glutamate, lithium acetate, sodium acetate, potassium acetate, calcium chloride (CaCl₂), strontium chloride (SrCl₂), manganese chloride (MnCl₂), and magnesium chloride (MgCl₂); polyols and sugars such as glycerol, erythritol, arabitol, sorbitol, mannitol, xylitol, mannisidomannitol, glycosyl glycerol, glucose, fructose, sucrose, trehalose, and isofluoroside; polymers such as dextrans, levans, and polyethylene glycol; and some amino acids and derivatives thereof such as glycine, alanine, alpha-alanine, arginine, proline, taurine, betaine, octopine, glutamate, sarcosine, y-aminobutyric acid, and trimethylamine N-oxide ("TMAO") (see also e.g., Fisher et al. U.S. 20110053795, incorporated herein by reference in its entirety). In one embodiment, the present invention utilizes a solution comprising an osmolyte, wherein the osmolyte is an ionic salt. Those of ordinary skill in the art will appreciate other compounds that are suitable osmolytes for use in the present invention. In another aspect, the present invention provides solutions comprising two or more different osmolytes.

The architecture of the nanopore-based sequencing chip described herein comprises an array of wells (e.g., FIG. 5) having a volume of between 1 attoliter and 1 nanoliter.

As shown in FIG. 5, a membrane is formed on the top surfaces of dielectric layer 504 and spans across well 505. For example, the membrane includes a lipid monolayer 518 formed on top of hydrophobic layer 520. As the membrane reaches the opening of well 505, the lipid monolayer transitions to a lipid bilayer 514 that spans across the opening of the well. The lipid monolayer 518 may also extend along all or a part of the vertical surface (i.e., side wall) of a dielectric layer 504. In one embodiment, the vertical surface 504 along which the monolayer 518 extends comprises a hydrophobic layer. A bulk electrolyte 508 containing protein nanopore transmembrane molecular complexes (PNTMC) and the analyte of interest is placed directly above the well. A single PNTMC/nanopore 516 is inserted into lipid bilayer 514. In one embodiment, insertion into the bilayer is by electroporation. Nanopore 516 crosses lipid bilayer 514 and provides the only path for ionic flow from bulk electrolyte 508 to working electrode 502.

Cell 500 includes a counter electrode (CE) 510, which is in electrical contact with the bulk electrolyte 508. Cell 500 may optionally include a reference electrode 512. In some embodiments, counter electrode 510 is shared between a plurality of cells, and is therefore also referred to as a common electrode. The common electrode can be configured to apply a common potential to the bulk liquid in contact with the nanopores in the measurements cells. The common potential and the common electrode are common to all of the measurement cells.

In some embodiments, working electrode 502 is a metal electrode. For non-faradaic conduction, working electrode 502 may be made of metals that are resistant to corrosion and oxidation, e.g., platinum, gold, titanium nitride and graphite. For example, working electrode 502 may be a platinum electrode with electroplated platinum. In another example, working electrode 502 may be a titanium nitride (TiN) working electrode.

As shown in FIG. 5, nanopore 516 is inserted into the planar lipid bilayer 514 suspended over well 505. An electrolyte solution is present both inside well 505, i.e., trans side, (see salt solution 506) and in a much larger external reservoir 522, i.e., cis side, (see bulk electrolyte 508). The bulk electrolyte 508 in external reservoir 522 is above multiple wells of the nanopore-based sequencing chip. Lipid bilayer 514 extends over well 505 and transitions to lipid monolayer 518 where the monolayer is attached to hydrophobic layer 520. This geometry both electrically and physically seals well 505 and separates the well from the larger external reservoir. While neutral molecules, such as water and dissolved gases, may pass through lipid bilayer 514, ions may not. Nanopore 516 in lipid bilayer 514 provides a single path for ions to be conducted into and out of well 505.

For nucleic acid sequencing, a polymerase is attached to nanopore 516. A template of nucleic acid (e.g., DNA) is held by the polymerase. For example, the polymerase synthesizes DNA by incorporating hexaphosphate mono-nucleotides (HMN) from solution that are complementary to the template. A unique, polymeric tag is attached to each HMN. During incorporation, the tag threads the nanopore aided by an electric field gradient produced by the voltage between counter electrode 510 and working electrode 502. The tag partially blocks nanopore 516, procuring a measurable change in the ionic current through nanopore 516. In some embodiments, an alternating current (AC) bias or direct current (DC) voltage is applied between the electrodes.

Nucleic acid sequencing using the nanopore-based sequencing chip includes steps in which different types of fluids (e.g., liquids or gases) are flowed through the cells of the nanopore-based sequencing chip via a flow chamber. Multiple fluids with significantly different properties (e.g., compressibility, hydrophobicity, and viscosity) are flowed over an array of sensors on the surface of the nanopore-based sequencing chip. For improved efficiency, each of the sensors in the array should be exposed to the fluids in a consistent manner. For example, each of the different types of fluids should be flowed over the nanopore-based sequencing chip such that the fluid may be delivered to the chip, evenly coating and contacting each of the cells' surfaces, and then delivered out of the chip. As described above, a nanopore-based sequencing chip incorporates a large number of sensor cells configured as an array. As the nanopore-based sequencing chip is scaled to include more and more cells, achieving an even flow of the different types of fluids across the cells of the chip becomes more challenging.

Figure 6:
FIG. 6 illustrates the top view of a nanopore-based sequencing system 600 with a flow chamber enclosing a silicon chip that allows liquids and gases to pass over and contact sensors on the chip surface.

In some embodiments, the nanopore-based sequencing system includes a flow chamber having a serpentine fluidic flow channel that directs the fluids to traverse over different sensors of the chip along the length of the channel. The flow channel can be used to contain the bulk electrolyte 114 in FIG. 1 and the bulk electrolyte 508 in FIG. 5. The flow channel can be used to form external reservoir 522 in FIG. 5. FIG. 6 illustrates the top view of a nanopore-based sequencing system 600 with a flow chamber enclosing a silicon chip that allows liquids and gases to pass over and make contact with the sensors on the chip surface. The flow chamber includes a serpentine or winding fluidic flow channel 608 that directs the fluids to flow directly above a single column (or a single row) of sensor banks 606 (each bank including several thousands of sensor cells) from one end of the chip to the opposite end and then directs the fluids to repeatedly loop back and flow directly above other adjacent columns of sensor banks, until all of the sensor banks have been traversed at least once. As shown in FIG. 6, system 600 includes an inlet 602 and an outlet 604.

With reference to FIG. 6, a fluid is directed into system 600 through inlet 602. The type of fluid, the concentration of the fluid, or the flow speed may be selected by a fluidic system that includes a processor for controlling the fluidic system and a fluidic pump for pumping the fluid into the inlet and out of the outlet. Inlet 602 may be a tube or a needle. For example, the tube or needle may have a diameter of one millimeter. Instead of feeding the liquid or gas directly into a wide flow chamber with a single continuous space, inlet 602 feeds the liquid or gas into a serpentine fluidic flow channel 608 that directs the liquid or gas to flow directly above a single column of sensor banks 606. The serpentine fluidic flow channel 608 may be formed by stacking together a top plate and a gasket with dividers 610 that divide the chamber into the serpentine channel to form a flow cell, and then mounting the flow cell on top of the chip. Once the liquid or gas flows through the serpentine fluidic flow channel 608, the liquid or gas is directed up through outlet 604 and out of system 600.

System 600 allows the fluids to flow more evenly on top of all the sensors on the chip surface. The channel width is configured to be narrow enough such that capillary action can take effect. More particularly, the surface tension (which is caused by cohesion within the fluid) and adhesive forces between the fluid and the enclosing surfaces act to hold the fluid together, thereby preventing the fluid or the air bubbles from breaking up and creating dead zones. For example, the channel may have a width of 1 millimeter or less. The narrow channel enables controlled flow of the fluids and minimizes the amount of remnants from a previous flow of fluids or gases.

Figure 7B:
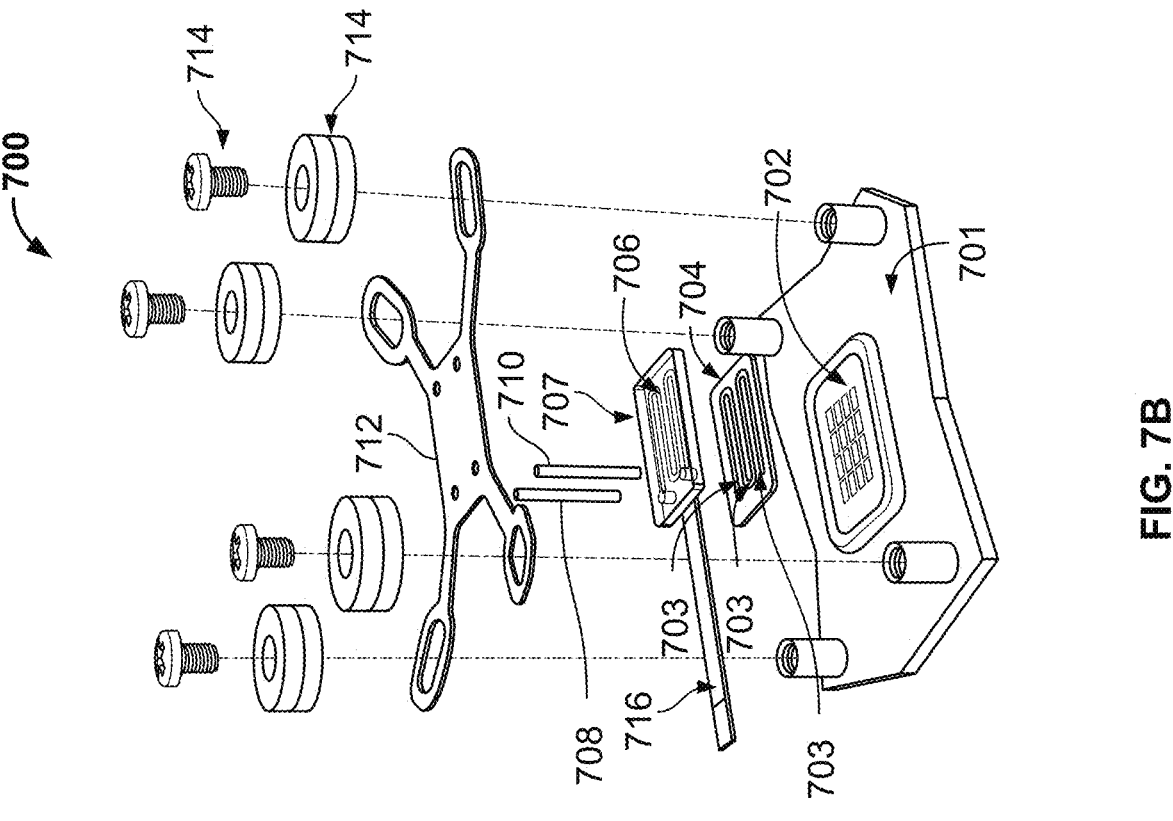
FIG. 7B illustrates the various components that are laminated together to form nanopore-based sequencing system 700.
Figure 7A:
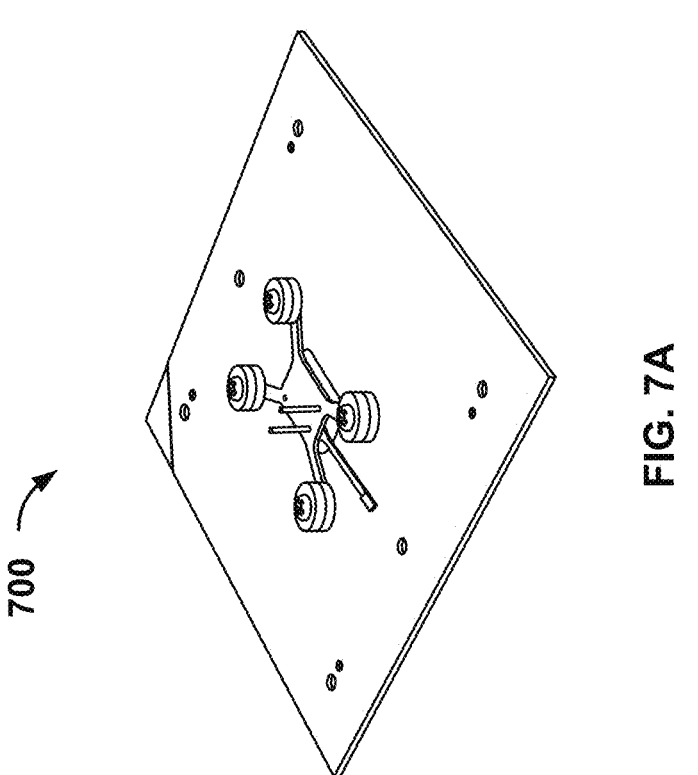
FIG. 7A illustrates an exemplary view of one embodiment of a nanopore-based sequencing system 700 with a serpentine fluidic flow channel.

FIG. 7A illustrates an exemplary view of one embodiment of a nanopore-based sequencing system 700 with a serpentine fluidic flow channel. FIG. 7B illustrates the various components that are laminated together to form nanopore-based sequencing system 700. System 700 includes various components, including a printed circuit board 701, a nanopore array chip 702, a gasket 704 with dividers 703, a backing plate 707, a counter electrode 706 on the underside of backing plate 707, a flexible flat circuit 716 connecting to counter electrode 706, an inlet 708, an outlet 710, a spring plate 712, and a plurality of fastening hardware 714. The serpentine fluidic flow channel is the space formed between backing plate 707, gasket 704, and nanopore array chip 702. The serpentine flow channel is formed by stacking together backing plate 707 and gasket 704 to form a flow cell, and then mounting the flow cell on top of nanopore array chip 702. Additional embodiments of the flow channel may be found in Yuan, U.S. 20160274082, which is incorporated herein by reference in its entirety.

To increase sequencing throughput, the nanopore-based sequencing chip needs to be scaled to include more and more cells, upwards of millions or tens of millions of cells. However, a chip that includes millions of cells may quickly reach the maximum chip size allowed by the reticle sizes in the semiconductor industry. Brute force semiconductor scaling of the nanopore-based sequencing chip may not be achievable due to a number of reasons. As shown in FIG. 5, well 505 includes a volume of salt solution 506 above working electrode 502. The well dimensions cannot be easily reduced because each well needs to hold a certain amount of salt solution for the sequencing process to operate properly. Furthermore, the spacing between the wells cannot be easily reduced because reducing the spacing may introduce cross-talk between the cells. In addition, each cell includes analog measurement components (e.g., analog-to-digital converters (ADCs)) that cannot be easily scaled down in size. Another motivation is to reduce the cost of a nanopore-based sequencing package having a greater number of cells. Yet another goal is to shorten the design cycle and lower the cost when the number of cells in the system is changed based on product requirements. Therefore, improved techniques for increasing the number of cells in a nanopore-based sequencing system/package would be desirable.

In the present application, a multi-chip nanopore-based sequencing system that includes a plurality of nanopore-based sequencing chips and one or more flow cells integrated into a single package is disclosed. The multi-chip nanopore-based sequencing system has a number of advantages. The scaling of the number of cells in the package is not limited by a number of factors, including the maximum die size allowed by the reticle sizes in the semiconductor industry, the minimum well size and spacing, and different analog components' minimum sizes. The multi-chip nanopore-based sequencing package is also more cost-effective, because the number of cells may be scaled up without increasing the die size, which may lead to a lower percentage yield. The design cycle is significantly reduced because there is no need to redesign the silicon or the assembly process in order to change the number of cells in the package. The number of cells in the system may be increased by simply increasing the number of modular design units integrated into the system. For example, each design unit is a tile that may be independently assembled, and the tiles may be assembled side by side. Because of the shortened design cycle, the number of cells per package may be customized to provide a wider range of products at a relatively low cost.

Figures 8A, 8B:
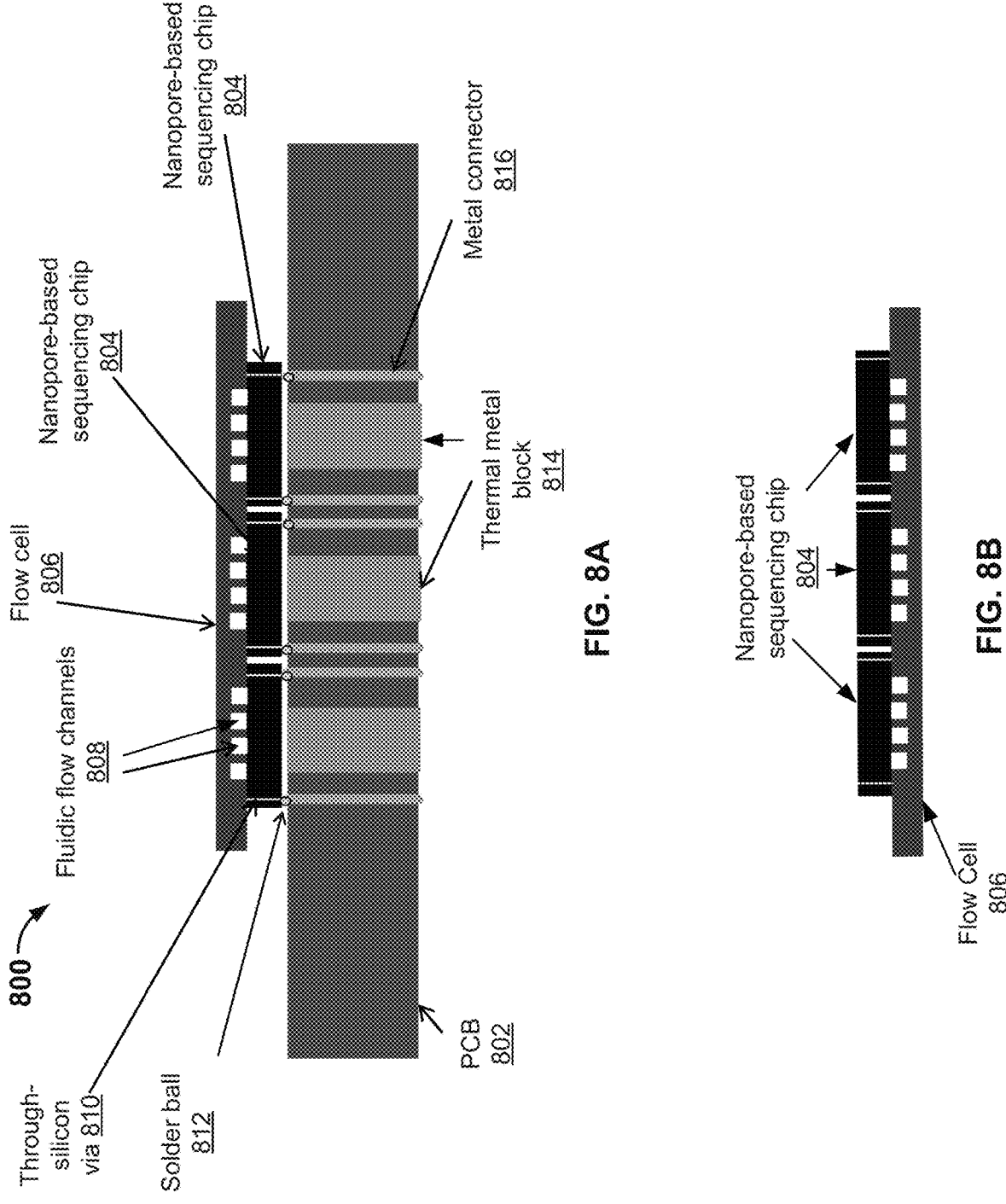
FIG. 8A illustrates an embodiment of a multi-chip nanopore-based sequencing system 800 that includes a plurality of nanopore-based sequencing chips integrated with a flow cell into a single system.
FIG. 8B illustrates an example of bonding the nanopore-based sequencing chips to the flow cell first.

FIG. 8A illustrates an embodiment of a multi-chip nanopore-based sequencing system 800 that includes a plurality of nanopore-based sequencing chips integrated with a flow cell into a single system. FIG. 8A illustrates a cross-sectional view of the multi-chip nanopore-based sequencing system. System 800 includes a printed circuit board (PCB) 802, a plurality of nanopore-based sequencing chips 804, and a flow cell 806. As shown in FIG. 8A, system 800 includes three nanopore-based sequencing chips 804. However, it should be recognized that a different number of nanopore-based sequencing chips 804 may be integrated into system 800 to either scale up or down the total number of cells in the system.

Each nanopore-based sequencing chip 804 incorporates a number of sensor cells configured as an array. For example, an array of one million cells may include 1000 rows by 1000 columns of cells. In some embodiments, each nanopore-based sequencing chip 804 is a single wafer chip. In some embodiments, each nanopore-based sequencing chip 804 is a stacked-wafers chip (see e.g., Tian, U.S. 20150275287, which is incorporated herein by reference in its entirety). The different types of components of the chip, e.g., the analog, digital, and memory components, may be partitioned into two or more wafers that are stacked vertically to form the stacked-wafers nanopore based sequencing chip. For example, each stacked wafer includes a different type of component, e.g., analog components only or digital components only. One advantage of separating digital components and analog components into different wafers is that it eliminates the need for mixed-signal wafers on the chip, which are more expensive than analog wafers or digital wafers; further, analog and digital wafers can be individually designed with different types of technologies, e.g., 180 nm technology for analog design and 28 nm technology for digital design.

Flow cell 806 may be formed using different materials. In some embodiments, flow cell 806 is formed by stacking together a backing plate and a gasket. The gasket may be molded with a flexible, compressible, or pliable material, such as plastic or rubber. The space between the backing plate, gasket, and the chips forms the serpentine fluidic flow channels 808. This type of flow cell has been disclosed in FIGS. 6, 7A, and 7B and is referred to as a flexible-material molded flow cell. In some embodiments, flow cell 806 is formed with a non-flexible material, such as glass. The glass flow cell is molded to include a plurality of serpentine fluidic flow channels 808 that may direct fluids to pass over and make contact with the sensors on the chips' surfaces.

Printed circuit board 802 includes a plurality of thermal metal blocks 814 for thermally conducting heat away from the nanopore-based sequencing chips 804. Although FIG. 8A shows that there is a gap between each thermal metal block 814 and its corresponding chip 804, it should be recognized that the thermal metal block is actually in contact with the chip, thereby facilitating the removal of heat from the chip. Printed circuit board 802 also includes a plurality of metal connectors 816. Sensor signals and other information may be transmitted from the cells via a plurality of through-silicon vias 810 to the bottom surfaces of the chips. The signals and information are then further transmitted out of system 800 through the solder balls 812 and the metal connectors 816. Control signals may be similarly transmitted from an external processor or controller via the metal connectors 816, solder balls 812, and through-silicon vias 810 to the cells in the chips.

In some embodiments, the plurality of nanopore-based sequencing chips 804 are bonded to flow cell 806 first, and then the chips and PCB 802 are bonded together. FIG. 8B illustrates an example of bonding the nanopore-based sequencing chips to the flow cell first. FIG. 8B illustrates a cross-sectional view of the nanopore-based sequencing chips and the flow cell. Flow cell 806 is positioned at the bottom. Note that flow cell 806 in FIG. 8B is oriented upside down, as compared to the flow cell 806 in FIG. 8A. The plurality of nanopore-based sequencing chips are also oriented upside down, i.e., with the cells (e.g., cells 500) oriented upside down, and bonded to flow cell 806. After the chips 804 are bonded to flow cell 806, the chips and PCB 802 are then bonded together. One advantage of bonding the chips to the flow cell first is that the flow cell provides a flat bonding surface, which facilitates the bonding of the chips with the flow cell. A flow cell 806 that is formed with a glass material may be bonded to the chips using a laser bonding technique. Some bonding techniques may generate a lot of heat at the bonding area, which may cause damage to the circuitry or to other components on the chips. Accordingly, the chips are designed to include bonding surfaces (e.g., on the periphery of the chips) that do not include circuitry or other components.

In system 800, one flow cell 806 is shared between multiple nanopore-based sequencing chips 804. The advantage of using one flow cell 806 to direct the fluid to flow above the sensors of all the nanopore-based sequencing chips 804 in the system is that only one inlet, one outlet, and one fluidic pump are required for the entire system, thereby reducing the overall cost of the system. However, flowing the fluid across the chip-to-chip boundaries creates a number of challenges. To ensure that the fluid can flow smoothly via the serpentine fluidic flow channels 808 across the chip-to-chip boundaries, the chips 804 should be butted against each other, instead of having gaps in between as shown in FIGS. 8A and 8B. For example, the side wall of a first chip that is adjacent to the side wall of a second chip should be straight and flat, such that the side walls of the two chips may butt against each other closely. Vertical dicing techniques may be used to dice the nanopore-based sequencing chips from wafers, such that the side walls of the chips are vertical and flat. For example, plasma etching tools may be used. Furthermore, the chip-to-chip boundaries should be hermetically sealed to be airtight and exclude the passage of liquids. For example, the side walls of two chips that are adjacent to each other should be hermetically sealed. In some embodiments, the side walls of two adjacent chips are hermetically sealed by depositing a hermetic sealing material, such as chromium. Another way to ensure that the fluid can flow smoothly via the serpentine fluidic flow channels 808 across the chip-to-chip boundaries is to bond the chips to flow cell 806 first, and then bond the chips and PCB 802 together, as discussed above. The advantage of bonding the chips to the flow cell first is that the flow cell provides a flat bonding surface such that the chips may be aligned vertically at the same level, which facilitates the forming of a hermetical seal between each of the chip-to-chip boundaries.

Figure 9:
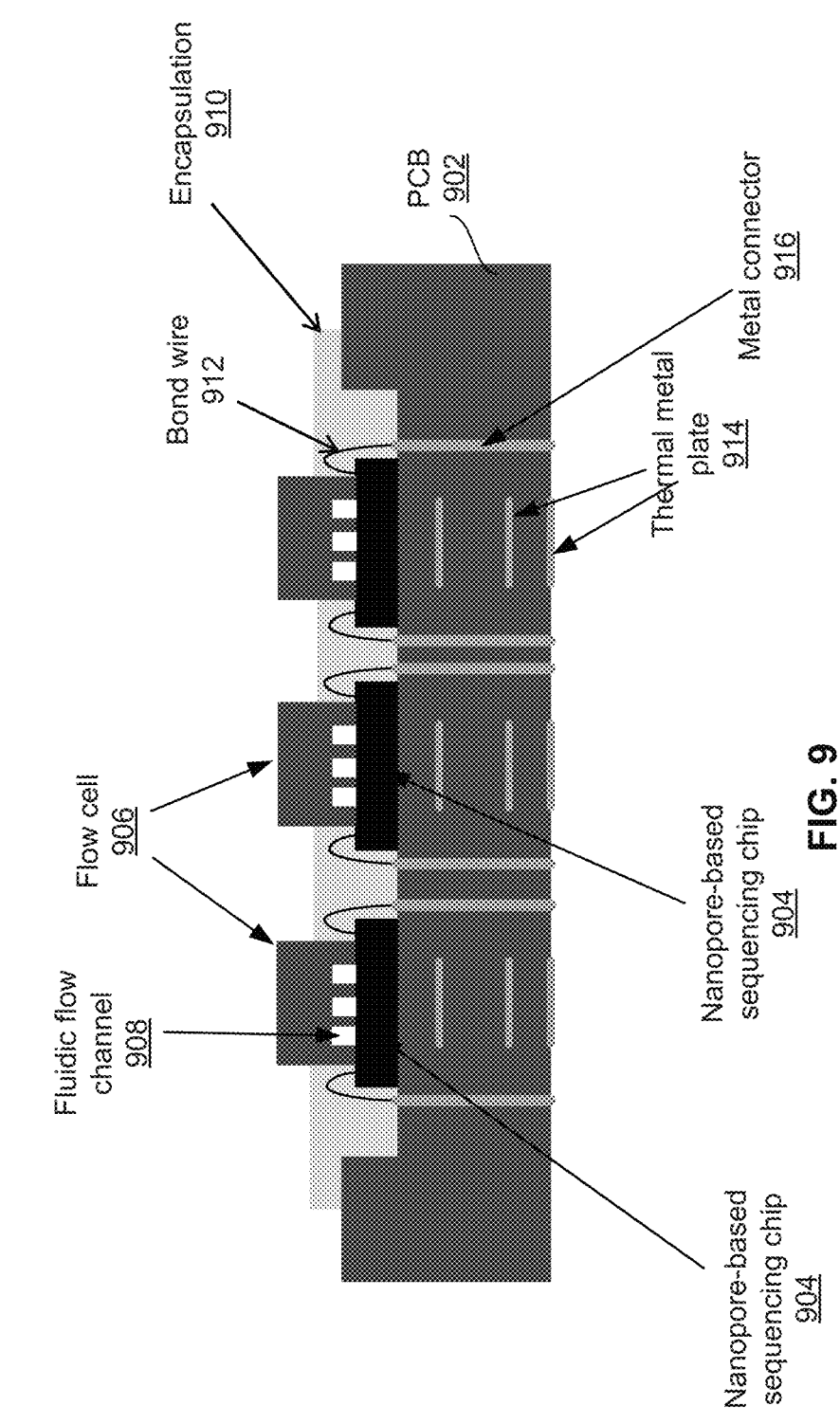
FIG. 9 illustrates an embodiment of a multi-chip nanopore-based sequencing system 900 that includes a plurality of nanopore-based sequencing chips integrated with a plurality of flow cells into a single system.

FIG. 9 illustrates an embodiment of a multi-chip nanopore-based sequencing system 900 that includes a plurality of nanopore-based sequencing chips integrated with a plurality of flow cells into a single system. FIG. 9 illustrates a cross-sectional view of the multi-chip nanopore-based sequencing system. System 900 includes a printed circuit board (PCB) 902, a plurality of nanopore-based sequencing chips 904, and a plurality of flow cells 906. As shown in FIG. 9, system 900 includes three nanopore-based sequencing chips 904. However, it should be recognized that a different number of nanopore-based sequencing chips 904 may be integrated into system 900 to either scale up or down the total number of cells in the system.

In some embodiments, each nanopore-based sequencing chip 904 is a single wafer chip. In some embodiments, each nanopore-based sequencing chip 904 is a stacked-wafers chip. The plurality of flow cells 906 may be a type similar to the flexible-material molded flow cell or glass flow cell as described in system 800, but instead of having a single flow cell to direct the fluid to flow above the sensors of all the chips in the system, system 900 includes one flow cell 906 for each chip 904, and each flow cell 906 has its own inlet, outlet, and fluidic pump. Each flow cell 906 includes a plurality of fluidic flow channels 908 to direct fluids to flow above the sensors of a single nanopore-based sequencing chip 904 in the system.

Printed circuit board 902 includes a plurality of thermal metal plates 914 for thermally conducting heat away from the nanopore-based sequencing chips 904. Alternatively, printed circuit board 902 may include a plurality of thermal metal blocks (not shown in FIG. 9), for example the type of thermal metal blocks shown in system 800, for thermally conducting heat away from the chips. Printed circuit board 902 also includes a plurality of metal connectors 916 for transmitting control or sensor signals and other information. Sensor signals and other information may be transmitted from the cells via a plurality of bond wires 912 to the metal connectors 916. The signals and information are then further transmitted through the metal connectors 916 to the bottom surface of PCB 902 and out of system 900. Control signals may be similarly transmitted from an external processor or controller via the metal connectors 916 and bond wires 912 to the cells in the chips.

In some embodiments, the plurality of nanopore-based sequencing chips 904 are bonded to PCB 902 first. After the chips 904 are bonded to PCB 902, bond wires 912 are used to electrically connect the chips 904 to the metal connectors 916 of PCB 902. In order to minimize the space on PCB 902 that is occupied by the chips 904, the chips are placed closely together. With the chips placed closely together, a bond wire technique is used to place the bond wires 912 that arch upwards and are very closely spaced together, while keeping the bond wires from touching each other.

The bond wires 912 are protected and covered by an encapsulation layer 910. Encapsulation layer 910 may be formed using different materials, such as epoxy. In some embodiments, the flow cells 906 are bonded to the chips 904 before encapsulation layer 910 is deposited. The advantage of placing the flow cells 906 before the encapsulation layer 910 is that the flow cells 906 may act as a dam that prevents the encapsulating material from being deposited onto the components of the chips. Some encapsulation processes are high-temperature processes, which may cause the flexible-material molded flow cells to melt. In this case, only flow cells that are made with materials that can withstand a high-temperature, e.g., glass, are used. Some encapsulation processes are not high-temperature processes. In this case, both the flexible-material molded flow cells or glass flow cells may be used. In some embodiments, the encapsulation process is a high-temperature process and the flexible-material moded flow cells are used. Because high temperatures may damage this type of flow cell, the encapsulation layer is deposited first and then the flow cells are secured on top of the chips by applying downward pressure on the tops of the flow cells.

Some bonding techniques for bonding the flow cells 906 to the chips 904 may generate a lot of heat at the bonding area, which may cause damage to the circuitry or other components on the chips. Accordingly, the chips 904 are designed to include bonding surfaces (e.g., on the periphery of the chips) that do not include circuitry or other components.

Figure 10:
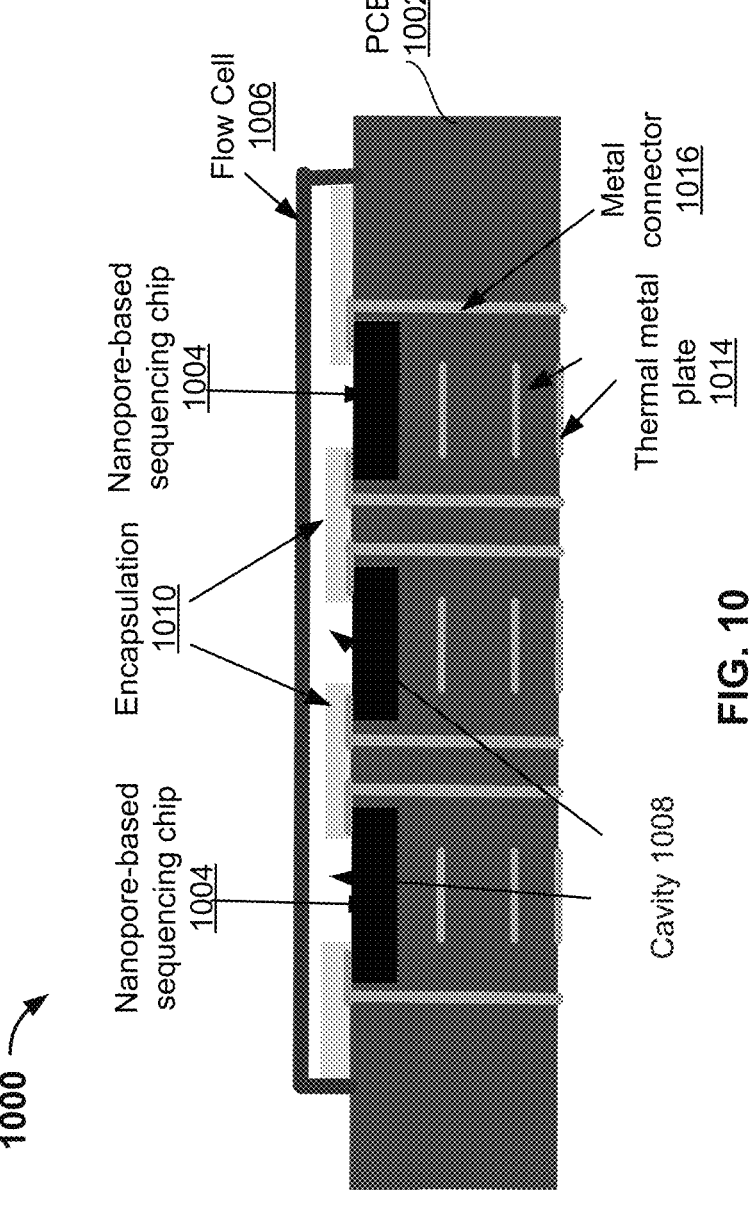
FIG. 10 illustrates an embodiment of a multi-chip nanopore-based sequencing system 1000 that includes a plurality of nanopore-based sequencing chips integrated with a flow cell into a single system.

FIG. 10 illustrates an embodiment of a multi-chip nanopore-based sequencing system 1000 that includes a plurality of nanopore-based sequencing chips integrated with a flow cell into a single system. FIG. 10 illustrates a cross-sectional view of the multi-chip nanopore-based sequencing system. System 1000 includes a printed circuit board (PCB) 1002, a plurality of nanopore-based sequencing chips 1004, and a flow cell 1006. As shown in FIG. 10, system 1000 includes three nanopore-based sequencing chips 1004. However, it should be recognized that a different number of nanopore-based sequencing chips 1004 may be integrated into system 1000 to either scale up or down the total number of cells in the system.

Printed circuit board 1002 includes a plurality of thermal metal plates 1014 for thermally conducting heat away from the nanopore-based sequencing chips 1004. Alternatively, printed circuit board 1002 may include a plurality of thermal metal blocks (not shown in FIG. 10)—for example, the type of thermal metal blocks shown in system 800—for thermally conducting heat away from the chips. Printed circuit board 1002 also includes a plurality of metal connectors 1016 for transmitting control or sensor signals and other information. Sensor signals and other information are transmitted from the cells of the chips through the metal connectors 1016 to the bottom surface of PCB 1002 and out of system 1000. Control signals may be similarly transmitted from an external processor or controller via the metal connectors 1016 to the cells in the chips.

In some embodiments, each nanopore-based sequencing chip 1004 is a single wafer chip. In some embodiments, each nanopore-based sequencing chip 1004 is a stacked-wafers chip. The nanopore-based sequencing chips 1004 are embedded within printed circuit board 1002. One of the advantages of embedding the chips 1004 within PCB 1002 is that bond wires (e.g., those used in system 900) for connecting the chips with the metal connectors 1016 of PCB 102 are not needed and may be replaced by the portions of the metal connectors 1016 that can lie flat on the top surfaces of PCB 1002 and the chips 1004, thereby saving vertical space and enabling the use of a single flow cell for the entire system. The advantage of using one flow cell 1006 to direct the fluid to flow above the sensors of all the nanopore-based sequencing chips 1004 in the system is that only one inlet, one outlet, and one fluidic pump are required for the entire system, thereby reducing the overall cost of the system.

Flow cell 1006 may be formed using different materials. In some embodiments, flow cell 1006 is formed with a non-flexible material, such as glass. The glass flow cell 1006 is molded to include a cavity 1008 or a plurality of fluidic flow channels (not shown in FIG. 10) that may direct fluids to pass over and make contact with the sensors on the chips' surfaces. A flow cell with a single big cavity, as opposed to a flow cell with multiple fluidic flow channels, has the advantage of simplifying the flow cell design and integration with the rest of the system. The portions of the metal connectors 1016 that are exposed on the top surfaces of the chips 1004 and PCB 1002 are covered by an encapsulation layer 1010, such that they are protected from the fluids in flow cell 1006. Encapsulation layer 1010 may be formed using different materials, such as epoxy. Encapsulating the metal connectors 1016 can be better controlled because the metal connectors 1016 provide a flatter surface than the bond wires in system 900.

In some embodiments, flow cell 1006 is formed by stacking together a backing plate and a gasket. The gasket may be molded with a flexible, compressible, or pliable material, such as plastic or rubber. The space between the backing plate, gasket, and the chips forms cavity 1008 or a plurality of fluidic flow channels (not shown in FIG. 10). In some embodiments, encapsulation layer 1010 is not a separately deposited layer, e.g., an epoxy layer, but is a portion of the gasket.

Flow cell 1006 is resting on top of PCB 1002 instead of the nanopore-based sequencing chips 1004. For a flow cell made with a flexible material, the flow cell is secured on top of PCB 1002 by applying downward pressure on the top of the flow cell. For a flow cell made with a non-flexible material, the flow cell may be bonded to PCB 1002 using a laser bonding technique. Some bonding techniques may generate a lot of heat at the bonding area. Since flow cell 1006 is bonded to PCB 1002 and not to the chips 1004, the bonding process will not damage the chips 1004 and the chips no longer need to have reserved bonding surfaces that do not include circuitries or other components, thereby saving a significant amount of the chips' surface area.

Figure 11:
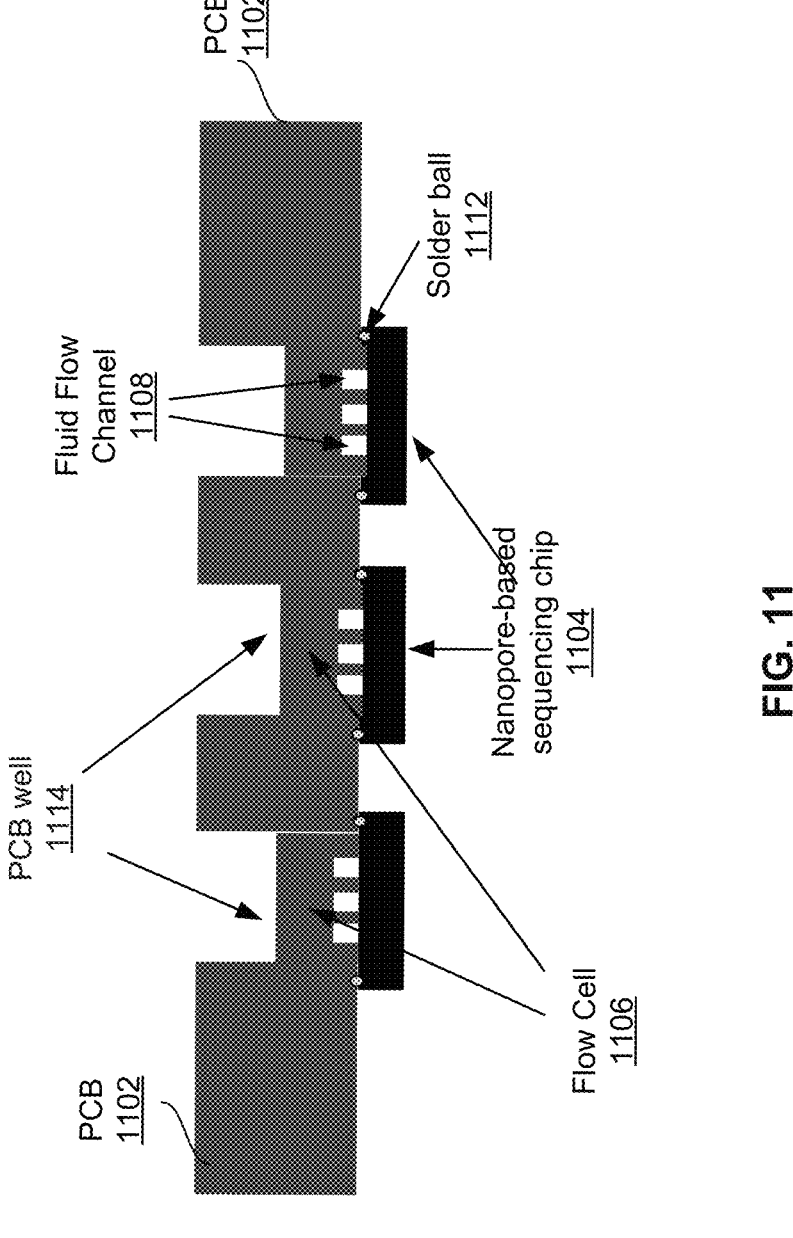
FIG. 11 illustrates an embodiment of a multi-chip nanopore-based sequencing system 1100 that includes a plurality of nanopore-based sequencing chips integrated with a plurality of flow cells into a single system.

FIG. 11 illustrates an embodiment of a multi-chip nanopore-based sequencing system 1100 that includes a plurality of nanopore-based sequencing chips integrated with a plurality of flow cells into a single system. FIG. 11 illustrates a cross-sectional view of the multi-chip nanopore-based sequencing system. System 1100 includes a printed circuit board (PCB) 1102, a plurality of nanopore-based sequencing chips 1104, and a plurality of flow cell 1106. As shown in FIG. 11, system 1100 includes three nanopore-based sequencing chips 1104. However, it should be recognized that a different number of nanopore-based sequencing chips 1104 may be integrated into system 1100 to either scale up or down the total number of cells in the system.

In some embodiments, each nanopore-based sequencing chip 1104 is a single wafer chip. In some embodiments, each nanopore-based sequencing chip 1104 is a stacked-wafers chip. As shown in FIG. 11, the nanopore-based sequencing chips 1104 are situated at the bottom, below the printed circuit board 1102. The advantage is that the chips 1104 may be in direct contact from below with a plurality of thermal metal blocks (not shown in FIG. 11) for thermally conducting heat away from the chips 804, which results in better temperature control of the system.

The plurality of flow cells 1106 may be a type similar to the flexible-material molded flow cell or glass flow cell as described in system 800, but instead of having a single flow cell to direct the fluid to flow above the sensors of all the chips in the system, system 1100 includes one flow cell 1106 for each chip 1104, and each flow cell 1106 has its own inlet, outlet, and fluidic pump. Each flow cell 1106 includes a plurality of fluidic flow channels 1108 to direct fluids to flow above the sensors of a single nanopore-based sequencing chip 1104 in the system.

Printed circuit board 1102 includes a plurality of cavities 1114. To assemble the system, each of the nanopore-based sequencing chips 1104 is positioned right-side up with the sensors facing upward, i.e., with the wells (e.g., well 505 of FIG. 5) right-side up. PCB 1102 is placed above the chips 1104 in such a way that the sensor arrays on the chips 1104 are exposed by the plurality of cavities 1114. With a chip 1104 placed on one of two openings of a cavity 1114, the chip 1104 together with the cavity 1114 forms a well in PCB 1102. A flow cell 1106 is then embedded in the well and bonded to the chip 1104 in such a way that the flow cell's fluidic flow channels 1108 may direct fluids to flow above the sensors of the chip 1104. In addition, solder balls 1112 provide the contacts between the chips 1104 and PCB 1102.

The multi-chip nanopore-based sequencing system disclosed in the present application may be further optimized by determining an optimal chip size based on the tradeoff between yield and reduced wasted bonding chip areas. If the nanopore-based sequencing chips are too large in size, then the chip yield due to semiconductor manufacturing decreases, thereby increasing silicon chip cost. If the nanopore-based sequencing chips are too small in size, then the percentage of chip areas used by bond wires and flow cell walls increases, thereby increasing silicon chip costs. Given the set of chip yield model and bond wire/flow cell design rules, the chip size may be optimized for the lowest chip cost.

The invention claimed is:

1. A nanopore-based sequencing device, comprising:
    a printed circuit board;
    a plurality of nanopore-based sequencing chips disposed on the printed circuit board, wherein the plurality of nanopore-based sequencing chips are electrically connected to the printed circuit board, wherein each of the nanopore-based sequencing chips comprises a plurality of nanopore sensors, each nanopore sensor configured to support a membrane and a nanopore that is inserted into the membrane, wherein each nanopore has a pore diameter suitable for nucleotide sequencing, wherein all the nanopores have the same pore diameter; and
    a flow cell disposed on the printed circuit board and over the plurality of nanopore-based sequencing chips, wherein the flow cell, when disposed over the plurality of nanopore-based sequencing chips, is configured to form a serpentine fluidic flow path that is configured to allow a fluid to flow over the plurality of nanopore-based sequencing chips along a serpentine path.

2. The nanopore-based sequencing device of claim 1, wherein the flow cell comprises a fluid inlet and a fluid outlet.

3. The nanopore-based sequencing device of claim 1, wherein the flow cell comprises a molded pliable material or glass material.

4. The nanopore-based sequencing device of claim 1, further comprising a plurality of bond wires, and wherein the printed circuit board further comprises a plurality of metal connectors, and wherein the plurality of bond wires electrically connect at least one of the plurality of nanopore-based sequencing chips to at least some of the plurality of metal connectors, and wherein the plurality of bond wires arch upwards and do not touch one another.

5. The nanopore-based sequencing device of claim 1, wherein the plurality of nanopore-based sequencing chips are embedded in the printed circuit board, and wherein the printed circuit board further comprises a plurality of metal connectors, and wherein at least one of the plurality of metal connectors has a portion that lies flat on a top surface of the printed circuit board and that lies flat on a top surface of one of the plurality of nanopore-based sequencing chips, and wherein the at least one of the plurality of metal connectors is electrically connected to the one of the plurality of nanopore-based sequencing chips.

6. The nanopore-based sequencing device of claim 1, wherein the printed circuit board comprises a plurality of cavities, and wherein the at least one of the plurality of nanopore-based sequencing chips is positioned right-side up and below the printed circuit board such that the plurality of nanopore sensors of the nanopore-based sequencing chip are exposed by one of the plurality of cavities.

7. The nanopore-based sequencing device of claim 1, wherein each of the nanopore-based sequencing chips comprises a plurality of banks, wherein each bank comprises a plurality of nanopore sensors.

8. The nanopore-based sequencing device of claim 1, wherein each of the nanopore-based sequencing chips are made from a discrete piece of silicon.

9. A nanopore-based sequencing device, comprising:
a printed circuit board;
a plurality of nanopore-based sequencing chips disposed on the printed circuit board, wherein the plurality of nanopore-based sequencing chips are electrically connected to the printed circuit board, wherein each of the nanopore-based sequencing chips comprises a plurality of nanopore sensors, each nanopore sensor configured to support a membrane and a nanopore that is inserted into the membrane, wherein each nanopore has a pore diameter suitable for nucleotide sequencing, wherein all the nanopores have the same pore diameter; and
a flow cell disposed on the printed circuit board and over the plurality of nanopore-based sequencing chips.

10. The nanopore-based sequencing device of claim 9, wherein each of the nanopore-based sequencing chips comprises a plurality of banks, wherein each bank comprises a plurality of nanopore sensors.

11. The nanopore-based sequencing device of claim 9, wherein each of the nanopore-based sequencing chips are made from a discrete piece of silicon.

* * * * *